United States Patent [19]

Bousquet et al.

[11] Patent Number: 5,081,240
[45] Date of Patent: Jan. 14, 1992

[54] PROCESS FOR THE PREPARATION OF BENZOTHIAZEPIN-ONE DERIVATIVES

[75] Inventors: André Bousquet; Jean-Robert Dormoy; Alain Heymes, all of Sisteron, France

[73] Assignee: Sanofi, Paris, France

[21] Appl. No.: 551,265

[22] Filed: Jul. 12, 1990

[30] Foreign Application Priority Data

Jul. 18, 1989 [FR] France .................. 8909645

[51] Int. Cl.$^5$ .................. C07D 281/10; A61K 31/55
[52] U.S. Cl. .................. 540/491; 562/60; 549/549
[58] Field of Search .......... 562/90; 549/549; 514/211; 540/491

[56] References Cited

FOREIGN PATENT DOCUMENTS 2139620 11/1984 United Kingdom ............. 540/491

OTHER PUBLICATIONS

Tetrahedron Letters, vol. 27, No. 44, 1986, pp. 5397–5400, Pergamon Journals Ltd, GB; H. Akita et al., "Determination of absolute structure of (−)-oudemansin B".

Journal of the Chemical Society, Perkin Transactions II, No. 10, 1973, pp. 1480–1490.

*Primary Examiner*—Robert T. Bond
*Attorney, Agent, or Firm*—Wegner, Cantor, Mueller & Player

[57] ABSTRACT

The object of the invention is a process for the preparation of the trans(−) (2R,3S) diastereoisomer of the glycidic esters of general formula:

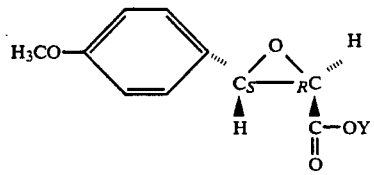

wherein a chlorohydrin of general formula:

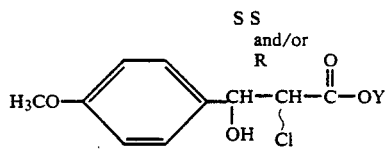

is reacted with a strong organic base in a suitable solvent and at a temperature between −10° C. and room temperature.

Another object of the invention is intermediate compounds cis(+) (2S,3S) 1,5-benzothiazepin-4-one.

2 Claims, No Drawings

PROCESS FOR THE PREPARATION OF BENZOTHIAZEPIN-ONE DERIVATIVES

In a general manner, the present invention relates to a new process for the preparation of glycidic esters, novel reaction intermediates as well as a new process for the preparation of benzothiazepin-one derivatives.

In particular, the invention relates to a new process for the preparation of the trans(−)(2R,3S) diastereoisomer of the glycidic esters of formula:

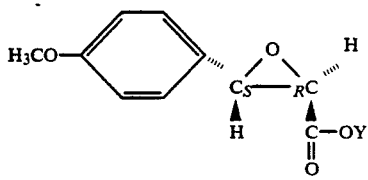

I in which Y denotes a $C_1$-$C_8$ alkyl radical.

By "$C_1$-$C_8$ alkyl" radical is meant linear or branched saturated hydrocarbon residues such as, for example, methyl, ethyl, n-propyl, isopropyl, n-butyl, isobutyl, tert.butyl, n-pentyl, n-hexyl, n-heptyl or n-octyl.

Y preferably represents the methyl radical.

The trans(−)(2R,3S) diastereoisomers of formula I constitute intermediate compounds particularly useful for the preparation in particular of cis-(+)(2S,3S) 2-hydroxy 3-(4-methoxyphenyl) 3-(2-amino phenylthio) propionic acid.

This acid, described in the patent FR-A-2 530 243, is a synthetic intermediate, the use of which according to the process of the French patent in question makes it possible to prepare cis(+)(2S,3S) diastereoisomeric derivatives of 1,5-benzothiazepin-4-one, known for their properties as calcium antagonists, hypotensives and coronary and cerebral vasodilators.

Such derivatives may be represented by the general formula:

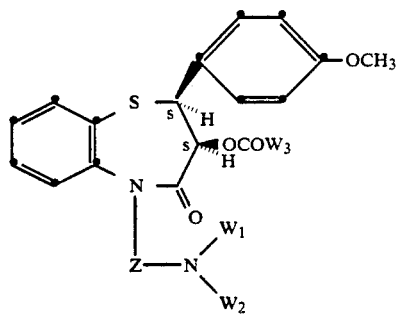

Ia in which $W_1$, $W_2$ and $W_3$, which are identical or different, each denotes a $C_1$-$C_4$ alkyl radical, preferably methyl, and Z represents a $C_1$-$C_4$ alkylene radical, preferably ethylene.

The most interesting 1,5-benzothiazepin-4-one derivative of this series is unquestionably cis(+)(2S,3S) 3-acetoxy 5-(2-N,N-dimethylamino ethyl) 2-(4-methoxyphenyl) 2,3-dihydro 1,5-benzothiazepin-4(5H)-one, commonly called diltiazem.

Most of the compounds presently known for the preparation of this compound involve non-sterospecific synthesis. According to these processes, the correct configuration of the 2 and 3 carbon atoms of diltiazem is attained by an optical resolution of the final compound or of one of the intermediates leading to the final compound. Thus, the resolution of threo(2SR,3SR) 2-hydroxy 3-(2-amino phenylthio) 3-(4-methoxyphenyl) propionic acid by means of, for example, d-α-phenylethylamine (patent application FR-A-2.530.243), lysine (patent application FR-A-2.534.579) or also d-p-tolylethylamine (patent application JP-A-85/243.062) has been considered.

Similarly, the resolution of threo(2SR,3SR) 2-hydroxy 3-(2-nitrophenylthio) 3-(4-methoxyphenyl) propionic acid and of threo(2SR,3SR) 2-hydroxy 3-(2-dimethylaminoethylamino phenylthio) 3-(4-methoxyphenyl) propionic acid by means of cinchonidine have been described (patent applications JP-A-78/018038 and JP-A-83/ 110685).

Finally, the optical separation of diltiazem itself by means of optically active mandelic acid (patent application JP-A-83/032873) or a chiral column (patent application JP-A-85/046111) has been performed.

Such an optical resolution step has an unfavourable effect on the yields which fall, in consequence, by at least 50%, the final yield of diltiazem being 25% at the very most.

Furthermore, these optical separations lead to an appreciable increase in the final cost of production of diltiazem since they are usually performed on quite complex intermediates in the context of the total synthesis.

Moreover, a process for the preparation of diltiazem, starting from a (−)(2R,3S) glycidic ester, obtained by optical resolution of the (±)(2RS,3SR) 2,3-epoxy 3-(4-methoxyphenyl) propionic acid with an optically active amine so as to recover an alkali metal salt of the trans(−)(2R,3S) 2,3-epoxy 3-(4-methoxyphenyl) propionic acid which is esterified to give a (−)(2R,3S) 2,3-epoxy 3-(4-methoxyphenyl) propionic ester, has been described in the patent applications JP-A-86/145159, JP-A-86/145160 and JP-A-86/145173.

This process, like its predecessors, also requires an optical resolution at the level of the glycidic intermediates.

Consequently, it appears advantageous to have available an industrial process capable of supplying the trans(−)(2R,3S) 2,3-epoxy 3-(4-methoxyphenyl) propionic esters of the patent application JP-A-61/145160 according to a stereospecific synthesis.

A widely known and widely used method for the preparation of epoxides is based on the Darzens reaction which consists of the cyclization in basic medium of halohydrins obtained from an aldehyde and an α-halogenated derivate.

Now, it is also well established that the step of either retroaldolization or cyclization of the halohydrins produced during this reaction is affected very considerably by the reaction medium and the reagents used such that is is impossible to predict with certainty the final result of such a reaction carried out starting from any halohydrin and a given basic reaction medium (J. Org. Chem., Vol. 34, No. 11, pp. 3600–3606).

For example, a synthesis has been described in Tetrahedron Letters 27 pp. 5397–5400 (1986) which enables a trans(2R,3S) diastereoisomer of a glycidic ester ultimately to be obtained. According to this process, the epoxidation of a mixture of optically active (2RS,3S) chlorohydrins, i.e. a mixture of (2RS,3S) ethyl 2-chloro 3-hydroxy butanoates, is carried out according to the Darzens reaction in order to produce an 85/15 mixture of ethyl trans/cis 2,3-epoxy butanoates, the reaction being performed in the presence of sodium ethylate in ethanol. The chemical yield of this reaction was found to be 84%.

After removal of the cis epoxide by transitory conversion to the brucine salt of the corresponding butanoic acid, the optically pure trans(2R,3S) 2-epoxy butanoic acid (enantiomeric excess >99%) was recovered in a yield of only 37%, which would suggest, in view of the nature of the salt, a resolution of a mixture of trans diastereoisomers.

Now, it has been found according to the invention that it is possible, starting from chlorohydrins in the form of a mixture of optically active (2RS,3S) diastereoisomers, to obtain trans(−)(2R,3S) diastereoisomers of 4-methoxy phenylglycidic esters in very high chemical yield since the enantiomeric excess (ee) is higher than 85% and does not require the intermediary formation of a salt.

According to the invention, the diastereoisomers of formula I are prepared by reacting a chlorohydrin of general formula:

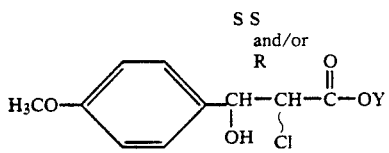

in which Y has the same meaning as before, with an organic base and in a suitable solvent.

A strong organic base, preferably 1,8-diazabicyclo [5,4,0] undec-7-ene, is usually used as base The solvent usually used is an apolar or slightly polar aprotic solvent such as dichloroethane, a polar aprotic solvent such as acetonitrile or even a polar protic solvent such as an alcohol, for example methanol.

However, it is preferable to use a protic or aprotic polar solvent in which the diastereoselectivity of the conversion proves to be best.

As for the reaction, it takes places at a temperature from −10° C. to room temperature, and preferably at a temperature between −10° C. and +10° C., which allows maximal diastereoselectivity.

The chlorohydrins of formula II may be in the form either of a mixture of anti(+)(2S,3S) and syn(−)(2R,3S) diastereoisomers, or the anti(+)(2S,3S) diastereoisomer, or the syn(−)(2R,3S) diastereoisomer.

In the particular case of mixtures of methyl anti(+)(2S,3S) and syn(−)(2R,3S) 2-chloro 3-hydroxy 3-(4-methoxyphenyl) propionates, for example a 61/39 mixture, the formation of only the trans glycidic ester is observed in a chemical yield which may attain 100% and which exists predominantly in the form of the trans(−)(2R,3S) diastereoisomer since the enantiomeric excess is of the order of 86 to 88%.

In view of the enantiomeric excess of the starting chloro-hydrins, this result attests to excellent optical retention.

These results are all the more surprising since the bromo-hydrin analogues of the chlorohydrins of formula II were only able to provide the corresponding cis/trans mixture of epoxides of formula I, evidently without the occurrence of epimerization.

Furthermore, it has been observed that the conversion, for example, into methyl trans(−)(2R,3S) 2,3-epoxy 3-(4-methoxyphenyl) propionate can be achieved by using methyl anti(+)(2S,3S) 2-chloro 3-hydroxy 3-(4-methoxyphenyl) propionate in enantiomeric excess greater than 85% in order to give quantitatively and unequivocally the trans (−)(2R,3S) ester in question in an enantiomeric excess of 80 to 85%.

Similarly, it is possible to prepare the same trans(−)(2R,3S) ester starting from methyl syn(−)(2R,3S) 2-chloro 3-hydroxy 3-(4-methoxyphenyl) propionate in enantiomeric excess of 80 to 85% in order to give the trans(−)(2R,3S) ester in question in a yield of the order of 90% and in an enantiomeric excess of about 85%.

Consequently, these results demonstrate:

retention of the absolute configuration at carbon atom 3 of the chlorohydrins of formula II, an observation which suggests that retrocondensation does not occur, the conversion of the syn(−)(2R,3S) chlorohydrin, after epimerization at carbon atom 2, into the trans(−)(2R,3S) glycidic ester at the expense of the cis(2S,3S) glycidic ester.

This presupposes sufficiently different kinetics of cyclocondensation for the two diastereoisomeric chlorohydrins syn(−) (2R,3S) and anti(+)(2S,3S) and epimerization kinetics superior than those for the cyclocondensation into the cis epoxide.

The chlorohydrins of formula II, whether they are in the form of a mixture (2RS,3S) or the separated diastereoisomers (2S,3S) and (2R,3S) consequently constitute particularly interesting novel intermediates since they can give rise easily and in high yield to the glycidic esters of formula I, which are themselves useful for the final synthesis of the compounds of formula Ia and, in particular, diltiazem.

A second object of the invention consequently consists in the chlorohydrins of formula II in the form of anti(+)(2S,3S) diastereoisomers, syn(−)(2R,3S) diastereoisomers or in the form of their mixtures, as new intermediates which are useful in particular for the final preparation of the compounds of formula Ia and in particular diltiazem.

In particular, the invention relates to the chlorohydrins of formula II below:

Methyl anti(+)(2S,3S) 2-chloro 3-hydroxy 3-(4-methoxyphenyl) propionate

Methyl syn(−)(2R,3S) 2-chloro 3-hydroxy 3-(4-methoxyphenyl) propionate, as well as their mixtures.

The chlorohydrins of formula II can be obtained in the following manner:

a) p-methoxyacetophenone is reacted at reflux in a suitable solvent such as an aprotic solvent, for example benzene, toluene or xylene, and in the presence of a basic agent such as an alkali metal hydride, for example sodium hydride, with a compound of general formula:

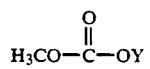

in which Y has the same meaning as before, which leads to the formation of a β-ketoester of general formula:

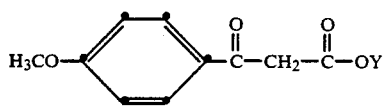

in which Y has the same meaning as before, b) the β-ketoester of formula IV is then treated with sulfuryl chloride at room temperature and in a suitable solvent, for example an aprotic solvent such as benzene, toluene or xylene, which leads to the formation of a α-chloro β-ketoester of general formula:

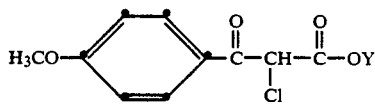

in which Y has the same meaning as before c) a stereoselective reduction of the α-chloro β-ketoester of formula V is then carried out according to the method described in J. Chem. Soc. Chem. Commun. (1985), pp. 138-139 and J. Organometallic Chem. (1985) 290 C23-C25, i.e. by treating the compound of formula V in question at a temperature between −70° C. and −40° C. with a mixture of (R,R) N,N'-dibenzoylcystine, tert.butanol and lithium borohydride in tetrahydrofuran, then by decomposing the complex formed by the addition of a strong acid such as hydrochloric acid, which leads to the formation of a mixture of about 50/50 of the syn and anti diastereoisomers of formula II in which the diastereoisomers syn(−)(2R,3S) very largely predominate.

If necessary, this mixture of syn(−)(2R,3S) and anti(+)(2S,3S) diastereoisomers can be separated into its constituents according to known techniques, such as by chromatography.

As for the the (R,R) N,N'-dibenzoylcystine, this latter can be prepared from (R)-cystine according to a protocol described in J. Med. Chem. (1969) pp. 950-953.

As indicated previously, the trans(−)(2R,3S) diastereoisomers of formula I can be used for the final synthesis of the cis(+)(2S,3S) derivatives of formula Ia and, in particular, diltiazem.

A third objective of the invention is consequently, a process for the preparation of the cis(+)(2S,3S) derivatives of formula Ia starting from the trans(−)(2R,3S) diastereoisomers of formula I, themselves obtained from the chlorohydrins of formula II according to the invention.

For this purpose, the process consists of the following steps:

a) the trans(−)(2R,3S) diastereoisomer of formula I obtained according to the invention from the chlorohydrins of formula II is reacted with 2-aminothiophenol to give a cis(+)(2S,3S) 2-hydroxy 3-(4-methoxyphenyl) 3-(2-amino phenylthio) propionic ester of general formula:

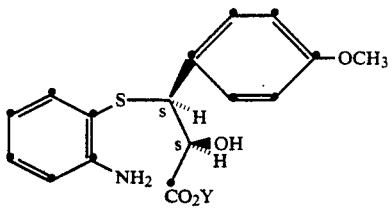

in which Y has the same meaning as before, b) the compound of formula VI is saponified by means of a basic agent such as an alkali metal hydroxide, for example sodium hydroxide or an alkali metal carbonate such as potassium carbonate, in order to form cis(+)(2S,3S) 2-hydroxy 3-(4-methoxyphenyl) 3-(2-amino phenylthio) propionic acid.

c) the cis(+)(2S,3S) 2-hydroxy (3-(2-amino phenylthio) propionic acid thus obtained is cyclized by heating at a temperature between 100° and 140° C. in an aromatic hydrocarbon, for example toluene, xylene or ethylbenzene, which leads to the formation of cis(+)(2S,3S) 3-hydroxy 2-(4-methoxyphenyl) 2,3-dihydro 1,5-benzothiazepin-4(5H)-one of formula:

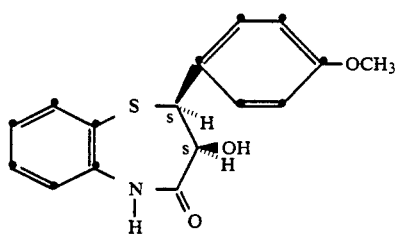

d) the cis(+)(2S,3S) derivative of formula VII is reacted with a halogen of general formula:

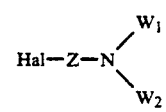

in which Hal denotes a halogen atom, for example chlorine, and $W_1$, $W_2$ and Z have the same meanings as before, or with a salt of this halogen, the halogen being preferably chlorine and the salt the hydrochloride, in the presence of a basic agent, for example potassium hydroxide, carbonate or bicarbonate and in a polar solvent, for example, formamide, acetamide, N,N-dimethylformamide or N,N-dimethylacetamide, in order to form the cis(+)(2S,3S) derivatives of 1,5-benzothiazepin-4-one of general formula:

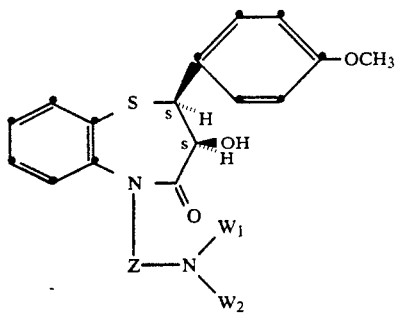

in which $W_1$, $W_2$ and Z have the same meanings as before, e) the cis(+)(2S,3S) derivative of 1,5-benzothiazepin-4-one of formula IX is reacted in an aprotic solvent such as an aromatic hydrocarbon at reflux with a suitable acylating agent, for example an anhydride of general formula:

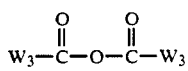

or an acid of formula:

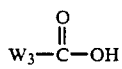

in which $W_3$ has the same meaning as before, in order to form the cis(+)(2S,3S) diastereoisomeric derivatives of 1,5-benzothiazepin-4-one of formula Ia in the form of the free base, the latter being allowed to react, if necessary, with a suitable inorganic or organic acid in order to form a pharmaceutically acceptable salt.

The following non-limiting examples illustrate the invention:

PREPARATION

Methyl anti(+)(2S,3S) and syn(−)(2R,3S) 2-chloro 3-hydroxy 3-(4-methoxyphenyl) propionates.

a) Methyl 3-(4-methoxyphenyl) 3-oxo propionate 51 g (1.064 mole) of 50% sodium hydride (previously washed twice with 100 ml of hexane), 340 ml of toluene and 90 ml (1.064 mole) of dimethylcarbonate are introduced under an argon atmosphere into a 2 l reactor equipped with a mechanical stirrer, a thermometer, a condenser and a dropping funnel. The reaction mixture is heated to reflux and then 80 g (0.532 mole) of p-methoxy-acetophrenone dissolved in 180 ml of toluene are added gradually during 2 hours.

After the addition is complete, the reaction mixture is refluxed for a further 15 minutes, cooled and then 35 ml of acetic acid and 150 ml of water (pH=5) are added successively. After being left to stand and separation by decantation, the aqueous phase is again extracted with 80 ml of toluene. The organic phases are combined, washed with 50 ml of a saturated solution of sodium bicarbonate, dried over sodium sulfate, and then evaporated to dryness. A thick oil is thus obtained (54.3 g) which crystallizes when a seed of methyl 3-(4-methoxyphenyl) 3-oxo propionate is added.

In this manner, methyl 3-(4-methoxyphenyl) 3-oxo propionate is obtained in a yield of 98% and may be purified by passage through a column of silica.

M.p.: 40.3° C.

Nuclear magnetic resonance spectrum (N.M.R.) (CDCl$_3$): 7.9 ppm (d,2H); 6.9 ppm (d,2H); 3.95 ppm (s,2H); 3.85 ppm (s,3H); 3.75 ppm (s,3H).

b) Methyl 2-chloro 3-(4-methoxyphenyl) 3-oxo propionate 24.96 g (0.12 mole) of methyl 3-(4-methoxyphenyl) 3-oxo propionate and 70 ml of anhydrous toluene are introduced into a 250 ml round bottomed flask equipped with a stirrer, a thermometer and a condenser, under an atmosphere of argon. 10.19 ml (0.126 mole) of sulfuryl chloride are added with stirring during 10 minutes while the temperature is mainained at 20° C. After the reaction mixture has been stirred for an additional 30 minutes at 20° C., 220 ml of a saturated aqueous solution of sodium bicarbonate (pH=7) are added, followed by 50 ml of toluene.

After separation of the phases by decantation, the toluene phase is dried over sodium sulfate and then concentrated in a vacuum.

In this manner, 28.24 g of methyl 2-chloro 3-(4-methoxyphenyl) 3-oxo propionate are obtained in a yield of 97% and can be purified by passage through a column of silica.

$n_D^{20} = 1.5630$.

N.M.R. spectrum (CDCl$_3$): 8–7.95 ppm (d,2H); 6.95–6.90 ppm (d,2H); 5.60 ppm (s,1H); 3.9 ppm (s,3H); 3.8 ppm (s,3H).

c) Methyl anti(+)(2S,3S) and syn(−)(2R,3S) 2-chloro 3-hydroxy 3-(4-methoxyphenyl) propionates 2.87 g (6.43 mmoles) of (R,R) N,N'-dibenzoyl-cystine, 32 ml of anhydrous tetrahydrofuran, 0.634 g of tert.butanol dissolved in 32 ml of anhydrous tetrahydrofuran and 19.3 ml of a 1M solution of lithium borohydride in tetrahydrofuran are introduced under an argon atmosphere into a 250 ml round bottomed flask equipped with a mechanical stirrer, thermometer, dropping funnel and condenser.

The white heterogeneous reaction mixture becomes homogeneous after being heated at reflux for 3 hours. The mixture is cooled to −70° C. and a solution of 1.3 g(5.36 mmoles) of methyl 2-chloro 3-(4-methoxyphenyl) 3-oxo propionate in 11 ml of tetrahydrofuran are added while the temperature of the reaction mixture is maintained at −70° C. The temperature of the reaction mixture is then allowed to rise to −40° C. and maintained there for 2 hours. Then 16.1 ml of 1N hydrochloric acid are added, causing the temperature to rise from −40° C. to 0° C., followed by 60 ml of water and 80 ml of dichloromethane.

After vigorous stirring of the mixture, the aqueous phase is isolated by decantation and extracted with 50 ml of methylene chloride. The organic phases are combined and then evaporated to dryness after being dried over sodium sulfate in order to obtain 3.60 g of a viscous product which is purified by rapid filtration through silica.

In this manner, 1.02 g of methyl 2-chloro 3-hydroxy 3-(4-methoxyphenyl) propionate are added in a yield of 77.8%. Syn diastereoisomer/anti diastereoisomer: 50/50 the diastereoisomeric excess of the product obtained is determined:

a) by thin layer chromatography (dichloromethane/ethyl acetate: 95/5) or by high performance liquid chromatography (H.P.L.C.) (detection 230 nm; flow rate 1.8 ml/min. eluant: water/methanol/acetonitrile/tetrahydrofuran: 770/50/180/10):
  syn diastereoisomer: 16.24 mn
  anti diastereoisomer: 25.56 mn
b) by proton N.M.R:

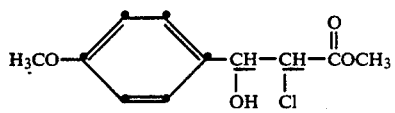

syn diastereoisomer: 5.1 ppm (d,1H); 4.42 ppm (d,1H)
anti diastereoisomer: 5 ppm (d,1H); 4.35 ppm (d,1H)

The two diastereoisomers syn and anti were separated by preparative high performance liquid chromatography. The enantiomeric excess of the diastereoisomers isolated was determined on the —CHH—OH proton by proton N.M.R. in $C_6D_6$ after addition of Eu $(tfc)_3$. The rotatory power was determined by polarimetry.

1) syn diastereoisomer (−)(2R,3S)
N.M.R.: two doublets located between 5.1 and 4.85±0.5 ppm.
ee: 841 %.
$α_D^{20}$: 2° C. (c=0.5, chloroform).

2) anti diastereoisomer (+)(2S,3S)
N.M.R.: two doublets located between 6.15 and 5.83±ppm.
ee: 88%.
$α_D^{20}$: +36° (c=0.5, chloroform).

EXAMPLE 1

Preparation of methyl trans(−)(2R,3S) 2,3-epoxy 3-(4-methoxyphenyl) propionate

Under an atmosphere of argon, 0.305 g (1.25 mmole) of methyl anti(+)(2S,3S) 2-chloro 3-hydroxy 3-(4-methoxyphenyl) propionate previously obtained ("Preparation") (ee=88%), 2.5 ml of dichloroethane and 0.2 ml (1.31 mmole) of 1,8-diazobicyclo [5.4.0] undec-7-ene are introduced into a 20 ml round bottomed flask, fitted with a thermometer, a condenser and a mechanical stirrer. A homogeneous reaction mixture is obtained.

After the mixture has been stirred for 2 hours at 20° C., the reaction is terminated. It is poured into 10 ml of a buffer solution (pH=7). After addition of 10 ml of dichloroethane, extraction and decantation, the organic phase is isolated and evaporated to dryness.

In this manner, 0.250 g of methyl trans(−)(2R,3S) 2,3-epoxy 3-(4-methoxyphenyl) propionate are obtained in crystalline form in a yield of 94.7%.

The presence of the cis epoxide was detected neither by N.M.R. nor by liquid chromatography.

N.M.R. (in dimethylsulfoxide)

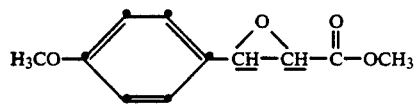

Trans diastereoisomer: 4.1 ppm (d,1H); 3.84 ppm (d,1H).
Cis diastereoisomer: 4.35 ppm (d,1H); 4 ppm (d,1H).

H. P. L. C.
a) Cis epoxide: 22.28 mn
Trans epoxide: 32,75 mn (detection: 230 nm; eluant: water: 770, methanol: 50, acetonitrile: 180, tetrahydrofuran: 10; flow rate: 1.8 ml/mn).

b) By means of liquid phase chromatography on a chiral column:
Eluant: isopropanol/hexane 50/50
Detection: 230 nm
Flow rate: 0.9 ml/mn
Trans(−) epoxide: 24.1 mn
Trans(+) epoxide: 20.6 mn
the enantiomeric excess of methyl trans(−)(2R.3S) 2,3-epoxy 3-(4-methoxyphenyl) propionate formed was determined: 88%.
Rotatory power
$α_D^{20}$ = −133° (c=0.892, chloroform).

Example 2

Preparation of methyl trans(−)(2R,3S) 2,3-epoxy 3-(4-methoxyphenyl) propionate

Under an argon atmosphere, 0.305 g (1.25 mmole) of syn(−)(2R,3S) 2-chloro 3-hydroxy 3-(4-methoxyphenyl) propionate previously obtained ("Preparation")(ee=84%), 2.5 ml of dichloroethane and 0.2 ml (1.31 mmole) of 1,8-diazobicyclo[5,4,0] undec-7-ene are introduced into a 20 ml round bottomed flask equipped with a thermometer, condenser and a mechanical stirrer.

A homogeneous reaction mixture is obtained. After it has been stirred for 2 hours at 20° C., the reaction is terminated. The mixture is then poured into 10 ml of a buffer solution (pH=7). After addition of 10 ml of dichloroethane, extraction and decantation, the organic phase is isolated and evaporated to dryness. Thus are obtained 0.260 g (yield: 96%) of a crystalline product constituted, according to the N.M.R. and the H.P.L.C., of 13% of cis epoxide and 87% of trans epoxide.

A separation by means of H.P.L.C. enabled methyl trans(−)(2R,3S) 2,3-epoxy 3-(4-methoxyphenyl) propionate to be isolated in the pure state.
ee: 84% (H.P.L.C.).

EXAMPLE 3

Preparation of methyl trans(−)(2R,3S) 2,3-epoxy 3-(4-methoxyphenyl) propionate

Under an atmosphere of argon, 0.78 of methyl syn(−)(2R,3S) 2-chloro 3-hydroxy 3-(4-methoxyphenyl) propionate (ee=70%), 1.22 g of methyl anti(+)(2R,3S) 2-chloro 3-hydroxy 3-(4-methoxyphenyl) propionate (ee=100%), 4 ml of dichloroethane and 1.32 ml of 1.8-diazabicyclo[5,4,0] undec-7-ene are introduced into a 50 ml round bottomed flask equipped with a thermometer, a condenser and a mechanical stirrer. A homogeneous reaction mixture is obtained. After it has been stirred for 2 hours at 20° C., the reaction is terminated. The reaction mixture is poured into 50 ml of a buffered solution (pH=7). After addition of 40 ml of dichloroethane, extraction and decantation, the organic phase is isolated, dried over sodium sulfate then evaporated to dryness to give an oil (1.72 g) which crystallizes (yield: 100%).

This product is a mixture of methyl trans(−)(2R,3S) 2,3-epoxy 3-(4-methoxyphenyl) propionate and methyl cis(+)(2S,3S) 2,3-epoxy 3-(4-methoxyphenyl) propionate.

Its diastereoisomeric composition was determined by proton N.M.R. and by H.P.L.C.

Trans diastereoisomer/cis diastereoisomer: about 95/5

A separation by means of H.P.L.C. enabled pure methyl trans (−)(23R,3S) 2,3-epoxy 3-(4-methoxyphenyl) propionate to be isolated. Trans(−) diastereoisomer/trans(+) diastereoisomer: 93.3/6.7 (ee=86.6%) (H.P.L.C.)

$\alpha_D{}^{23}$: −130°(c=0.9, chloroform)

EXAMPLE 4

Preparation of methyl trans(−)(2R,3S) 2,3-epoxy 3-(4-methoxyphenyl) propionate

Under an atmosphere of argon, 0.39 g of methyl syn(−)(2R,3S) 2-chloro 3-hydroxy 3-(4-methoxyphenyl) propionate (ee=70%) 0.610 g of methyl anti(+)(2S,3S) 2-chloro 3-hydroxy 3-(4-methoxyphenyl) propionate (ee=100% and 2 ml of methanol are introduced into a 50 ml round bottomed flask equipped with a thermometer and a mechanical stirrer. The mixture is cooled to −10° C. and 0.66 ml of 1,8-diazobicyclo [5,4,0] undec-7-ene are added. After being stirred for 4 hours at −5° C., the reaction mixture is evaporated to dryness. The oily residue is taken up in 25 ml of dichloroethane and the solution is washed with 25 of a buffered solution (pH=7). After extraction and decantation, the organic phase is isolated and evaporated to dryness to give 0.72 g of an oil which crystallizes (yield: 85%)

This product is a mixture of methyl trans(−)(2R,3S) 2,3-epoxy 3-(4-methoxyphenyl) propionate and methyl cis(+)(2S,3S) 2,3-epoxy 3-(4-methoxyphenyl) propionate. Its diastereoisomeric composition was determined by proton N.M.R. and by H.P.L.C.

Trans diastereoisomer/cis diastereoisomer: about 99/1.

A separation by means of H.P.L.C. enabled pure methyl trans(−) (2R,3S) 2,3-epoxy 3-(4-methoxyphenyl) propionate to be isolated. Trans(−) diastereoisomer/trans(+) diastereoisomer: 94/6 (ee=88%)

$\alpha_D{}^{23}$: −133° (c=0.9, chloroform).

EXAMPLE 5

Preparation of cis(+)(2S,3S) 3-acetoxy 5-(2-N,N-dimethylaminoethyl) 2-(4-methoxyphenyl) 2,3-dihydro 1,5-benzothiazepin-4-(5H)one hydrochloride or diltiazem hydrochloride a) Methyl cis(+)(2S,3S) 2-hydroxy 3-(2-amino phenylthio) 3-(4-methoxyphenyl) propionate Under an inert atmosphere, 13.875 g (0.111 mole) of o-amino-thiophenyl, 20.8 g (0.1 mole) of methyl trans(−)(2R,3S) 2,3-epoxy 3-(4-methoxyphenyl) propionate and 100 ml of toluene are placed in a 250 ml reactor equipped with a heating-cooling system, a mechanical stirrer, a thermometer and a condenser. The mixture is refluxed for 2 hours, then the toluene is distilled so as to give 34 g of a solid residue (mass yield: 100%).

In this manner, methyl cis(+)(2S,3S) 2-hydroxy 3-(2-amino phenylthio) 3-(4-methoxyphenyl) propionate is obtained which can be used directly in the next step or can be recrystalled from a methanol/water mixture so as to give an analytically pure compound.

b) Cis(+)(2S,3S) 2-hydroxy 3-(4-methoxyphenyl) 3-(2-amino phenylthio) propionic acid Under an inert atmosphere, 33.1 g (0.1 mole) of crude methyl cis(+)(2S,3S) 2-hydroxy 3-(2-amino phenylthio) 3-(4-methoxyphenyl) propionate and 160 ml of 5% sodium hydroxide are placed in a 250 ml round bottomed flask equipped with a heating-cooling system, a mechanical stirrer, a thermometer and a condenser. A mixture was heated to 50° C. under vigorous stirring and maintained at that temperature for 2 hours. The reaction mixture is limpid and brown. After being cooled to room temperature, the mixture is poured into 82 ml of 9% hydrochloric acid, which leads to the precipitation of the expected product. It is filtered off and washed with water, then dried in an oven under vacuum at 20° C.

In this manner, the cis(+)(2S,3S) 2-hydroxy 3-(4-methoxyphenyl) 3-(2-amino phenylthio) propionic acid is obtained in the crude state which can be purified by re-saponification in ethanol.

M.p.: 138° C.

$\alpha_D{}^{20}$: 346°.

c) Cis(+)(2S,3S) 2-hydroxy 2-(4-methoxyphenyl) 2,3-dihydro 1,5-benzothiazepin-4(5H)-one Under an inert atmosphere, 50 g (0.156 mole) of cis(+)(2S,3S) 2-hydroxy 3-(4-methoxyphenyl) 3-(2-amino phenylthio) propionic acid and 940 ml of xylene are placed in a 2 l reactor equipped with a heating-cooling system, a mechanical stirrer, a thermometer, a condenser and a Dean-Stark system. The mixture is brought to reflux and maintained there for 8 hours. It is cooled to −10° C., the solid is filtered off, washed with xylene and dried in a ventilated oven.

In this manner, 43 g of cis(+)(2S,3S) 3-hydroxy 2-(4-methoxyphenyl) 2,3-dihydro 1,5-benzothiazepin-4 (5H)-one.

Yield: 91%.

M.p.: 200° C.

$\alpha_D{}^{20}$: +115° C.

The filtrate contains a further 6 to 7% of the desired product which can be recovered.

d) Cis(+)(2S,3S) 3-hydroxy 5-(2-N,N-dimethylaminoethyl) 2-(4-methoxyphenyl) 2,3-dihydro 1,5-benzothiazepin-4(5H)-one Under an inert atmosphere, 12 g (0.04 mole) of cis(+)(2S,3S) 3-hydroxy 2-(4-methoxyphenyl) 2,3-dihydro 1,5-benzothiazepin-4(5H)-one and 60 ml of N,N-dimethylformamide are introduced into a 250 ml reactor equipped with a heating/cooling system, a mechanical stirrer, a thermometer and a condenser. The mixture is stirred and a limpid solution is obtained. Then 16.6 g (0.12 mole of potassium carbonate and 6.9 g (0.048 mole) of 2-dimethylamino 1-chloro-ethane hydrochloride are added. The mixture is heated at 60° C. for 1 hour. After the mixture has been cooled to room temperature, the mineral salts are filtered off and the filtrate is concentrated in a vacuum. The oily residue obtained is taken up in 75 ml of dichloroethane and washed with water. The organic phase is concentrated and the residue is taken up in petroleum ether so as to give rise to the crystallization of the expected product. It is filtered off and dried in an oven under vacuum.

In this manner, 13.65 g of cis(+)(2S,3S) 3-hydroxy 5-(N,N-dimethylaminoethyl) 2-(4-methoxyphenyl) 2,3-dihydro 1,5-benzothiazepin-4(5H)-one are obtained.

Yield: 91.6%.
M.p.: 86°–87° C.
$\alpha_D^{20}$: +168.8° (c=0.25, methanol).

e) Cis(+)(2S,3S) 3-acetoxy
5-(2-N,N-dimethylaminoethyl) 2-(4-methoxyphenyl)
2,3-dihydro 1,5-benzothiazepin-4(5H)-one
hydrochloride 5.6 g (0.015 mole) of cis(+)(2S,3S) 3-hydroxy 5-(2-N,N-dimethylaminoethyl) 2-(4-methoxyphenyl) 2,3-dihydro 1,5-benzothiazepin-4(5H)-one and 14 ml of anhydrous toluene are introduced into a 50 ml three-necked flask equipped with a heating/cooling system, a mechanical stirrer, a thermometer and a condenser. The mixture is stirred and 1.7 g (0.0165 mole) of acetic anhydride are added. The mixture is heated at the reflux temperature of toluene for 3 hours, then is cooled to room temperature and 3.4 ml of a 4.8N ethanolic solution of hydrogen chloride are added. The mixture is cooled to 0° C. and the precipitate obtained is filtered off. It is washed with toluene and dried.

In this manner, 6.25 g of cis(+)(2S,3S) 3-acetoxy 5-(2-N,N-dimethylaminoethyl) 2-(4-methoxyphenyl) 2,3-dihydro 1,5-benzothiazepin-4(5H)-one hydrochloride are obtained.

Yield: 92.4%.
M.p. 210° C.
$\alpha_D^{20}$: +116.5° (c=1%, water).

We claim:
1. A process for the preparation of cis(+) (2S,3S) diastereoisomeric derivatives of 1,5-benzothiazepin-4-one of general formula:

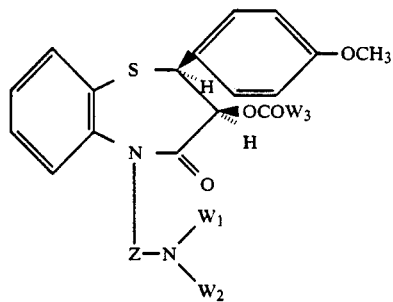

Ia in which $W_1$, $W_2$ and $W_3$, identical or different, each represents a $C_1$-$C_4$ alkyl radical and Z represents a $C_1$-$C_4$ alkylene radical, wherein:

a) a chlorohydrin of general formula:

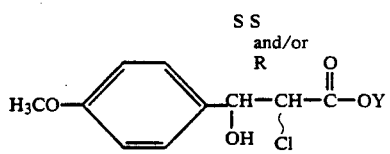

II in which Y denotes $C_1$-$C_8$ alkyl, is reacted with 1,8-diazobicyclo [5,4,0] undec-7-ene in a suitable solvent and at a temperature between −10° C. and room temperature in order to form the trans(−)(2R,3S) diastereoisomers of the glycidic esters of general formula:

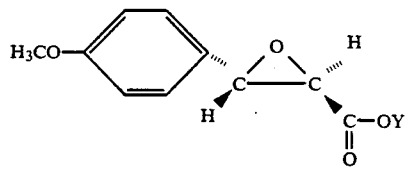

in which Y has the same meaning as before, b) the trans(−)(2R,3S) diastereoisomer thus obtained is reacted with 2-amino thiophenol to give a cis(+)(2S,3S) 2-hydroxy 3-(4-methoxyphenyl) 3-(2-amino phenylthio) propionic ester of general formula:

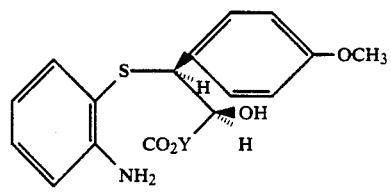

in which Y has the same meaning as before, c) the cis(+)(2S,3S) 2-hydroxy 3-(4-methoxyphenyl) 3-(2-amino phenylthio) propionic ester thus obtained is saponified by means of a basic agent in order to obtain the cis(+)(2S,3S) 2-hydroxy 3-(4-methoxyphenyl) 3-(2-amino phenylthio) propionic acid, d) the cis(+)(2S,3S) 2-hydroxy 3-(4-methoxyphenyl) 3-(2-amino phenylthio) propionic acid thus obtained is cyclized by heating at a temperature between 100° and 140° C. in an aromatic hydrocarbon, which leads to the formation of cis(+)(2S,3S) 3-hydroxy 2-(4-methoxyphenyl) 2,3-dihydro 1,5-benzothiazepin-4(5H)-one, e) this cis(+)(2S,3S) derivative of benzothiazepin is reacted with a halogen of general formula:

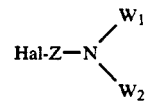

in which Hal represents a halogen atom and $W_1$, $W_2$ and Z have the same meanings as before, or with a salt of this halogen, in the presence of a basic agent and in a polar solvent to form the cis(+)(2S,3S) derivatives of 1,5-benzothiazepin-4-one of general formula:

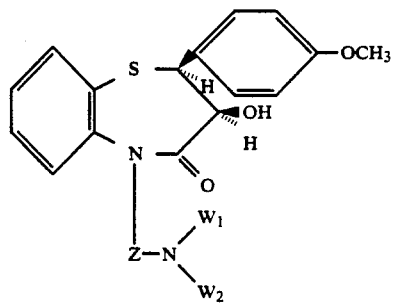

in which $W_1$, $W_2$ and Z have the same meanings as before.

f) the cis(+)(2S,3S) derivative of 1,5-benzothiazepin-4-one thus obtained is reacted with a suitable acylating agent selected from an anhydride of general formula:

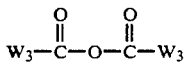

and an acid of general formula:

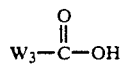

in which $W_3$ denotes a $C_1$-$C_4$ alkyl radical in order to form the desired cis(+)(2S,3S) diastereoisomeric derivatives of 1,5-benzothiazepin-4-one, which may be reacted, if desired, with a suitable inorganic or organic acid in order to prepare a pharmaceutically acceptable salt of this derivative.

2. The process of claim 1, wherein the cis(+)(2S,3S) diastereoisomer of formula Ia is prepared in which $W_1$, $W_2$ and $W_3$ each denotes methyl and Z represents ethylene.

* * * * *